US011525814B2

United States Patent
Li et al.

(10) Patent No.: US 11,525,814 B2
(45) Date of Patent: Dec. 13, 2022

(54) METHOD FOR SCREENING OF TOBACCO NICOTINE CONVERTERS

(71) Applicant: Yunnan Academy of Tobacco Agricultural Sciences, Kunming (CN)

(72) Inventors: Yong Li, Kunming (CN); Tao Pang, Kunming (CN); Xuejun Chen, Kunming (CN); Xueyi Sui, Kunming (CN); Junli Shi, Kunming (CN); Yongping Li, Kunming (CN); Guanghui Kong, Kunming (CN); Ping Chen, Kunming (CN); Yuping Wu, Kunming (CN)

(73) Assignee: YUNNAN ACADEMY OF TOBACCO AGRICULTURAL SCIENCES, Kunming (CN)

( * ) Notice: Subject to any disclaimer, the term of this patent is extended or adjusted under 35 U.S.C. 154(b) by 172 days.

(21) Appl. No.: 17/136,059

(22) Filed: Dec. 29, 2020

(65) Prior Publication Data

US 2021/0349063 A1 Nov. 11, 2021

(30) Foreign Application Priority Data

May 9, 2020 (CN) .......................... 202010385363.7

(51) Int. Cl.
*G01N 30/86* (2006.01)
*G01N 30/06* (2006.01)
(Continued)

(52) U.S. Cl.
CPC ......... *G01N 30/8679* (2013.01); *G01N 30/06* (2013.01); *G01N 30/7206* (2013.01);
(Continued)

(58) Field of Classification Search
CPC .............. G01N 30/8679; G01N 30/06; G01N 30/7206; G01N 30/8606; G01N 30/8637;
(Continued)

(56) References Cited

PUBLICATIONS

Shi, Hongzhi, et al. "Stimulation of nicotine demethylation by NaHCO3 treatment using greenhouse-grown burley tobacco." Journal of agricultural and food chemistry 51.26 (2003): 7679-7683. (Year: 2003).*

* cited by examiner

*Primary Examiner* — Jennifer Wecker
*Assistant Examiner* — Michael Paul Shimek
(74) *Attorney, Agent, or Firm* — Bayramoglu Law Offices LLC

(57) ABSTRACT

A method for identifying converters from tobacco seedling population. The method includes: 1) sowing and cultivating tobacco seeds to be identified for 45-55 days; sampling a plurality of leaf disks from each of 45-55 days old seedlings; 2) incubating the plurality of leaf disks of each seedling in a sealed container at 37° C. for 10-12 hours, thereby obtaining a plurality of incubated tobacco leaves of each seedling; 3) immersing the plurality of incubated tobacco leaves of each seedling in an extractant, extracting alkaloids and obtaining an extract of each seedling; 4) analyzing the amounts of nicotine and nornicotine in the alkaloids extract of each seedling; and 5) automatically recognizing peaks of the alkaloids extract of each seedling, and calculating the percent nicotine conversion (PNC) and the pseudo percent nicotine conversion (PPNC).

16 Claims, 5 Drawing Sheets

(51) Int. Cl.
*G01N 30/72* (2006.01)
*G01N 33/00* (2006.01)
*G01N 30/04* (2006.01)

(52) U.S. Cl.
CPC ..... *G01N 30/8606* (2013.01); *G01N 30/8637* (2013.01); *G01N 33/0098* (2013.01); *G01N 2030/042* (2013.01); *G01N 2030/062* (2013.01)

(58) Field of Classification Search
CPC ......... G01N 33/0098; G01N 2030/042; G01N 2030/062; G01N 2030/8886; G01N 30/02; G01N 30/8675; G01N 2030/045; G01N 2030/862; A24B 15/243; A01H 1/04
See application file for complete search history.

METHOD FOR SCREENING OF TOBACCO NICOTINE CONVERTERS

CROSS-REFERENCE TO RELATED APPLICATIONS

Pursuant to 35 U.S.C. § 119 and the Paris Convention Treaty, this application claims foreign priority to Chinese Patent Application No. 202010385363.7 filed May 9, 2020, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to the field of chemical detection and analysis technologies, and more particularly, to a method for screening of tobacco nicotine converters which convert a large part of their nicotine to nornicotine as their leaves maturing and being cured.

In the field of tobacco cultivation, a nicotine converter refers to a mutant strain of a tobacco plant capable of converting a large part of nicotine into nornicotine. Nornicotine is chemically similar to nicotine, but does not contain a methyl group. Nornicotine has a higher carcinogenic risk than nicotine.

A conventional method for identifying the converters from the normal tobacco plants include the use of chemical agents such as ethylene, ethephon, and sodium bicarbonate to convert nicotine into nornicotine, and then measure the percent conversion of nicotine. This method is time-consuming. The tobacco plants are cultivated in the chemical agents for 4-6 days, and the determination of nicotine and nornicotine in the tobacco leaves take several hours.

SUMMARY

The disclosure provides a method for identifying nicotine converters from a tobacco plant seedling population. The converters are capable of converting a large part of nicotine to nornicotine.

The method for identifying nicotine converters from tobacco plant population comprises: leaf sampling, sample incubation, alkaloids extraction, instrumental analysis, and data analysis.

Specifically, the method comprises:

S1. Leaf sampling: sowing and cultivating tobacco seeds to be identified in a greenhouse tray for 45-55 days: sampling a plurality of leaf disks from each of 45-55 days old seedling, where the plurality of leaf disks is identical to each other in size and shape;

S2. Sample incubation: incubating the plurality of leaf disks of each seedling in a sealed container at 37° C. for 10-12 hours, thereby obtaining a plurality of incubated tobacco leaves of each seedling:

S3. Alkaloids extraction: immersing the plurality of incubated tobacco leaves of each seedling in an extractant, extracting alkaloids and obtaining an extract of each seedling;

S4. Instrumental analysis: analyzing the amounts of nicotine and nornicotine in the alkaloids extract of each seedling by using a gas chromatography-mass spectrometry (GC-MS);

S5. Data analysis: automatically recognizing peaks of nicotine and nornicotine of each seedling using a GC-MS chemical workstation, calculating an integral of peak areas of the peaks, and calculating the percent nicotine conversion (PNC) and a pseudo percent nicotine conversion (PPNC) as follows:

$$PNC = \frac{C_{nornicotine}}{C_{nicotine} + C_{nornicotine}};$$

$$PPNC = \frac{A_{nornicotine}}{A_{nicotine} + A_{nornicotine}};$$

where C represents the concentration (mol/L) of nicotine or nornicotine, and A represents the peak area of nicotine or nornicotine; when the PNC or PPNC of a seedling is greater than or equal to a threshold value, the seedling is identified as a converter and removed from the seedling population: otherwise, the seedling is identified as a non-converter and retained.

The following advantages are associated with method of the disclosure:

1. The conventional converter identification technology uses stimulants (i.e., ethylene, ethephon, and sodium bicarbonate) to cultivate the tobacco leaves, so as to expand the difference of the PNCs of the converters and non-converters. The process requires appropriate temperature and moisture, and takes several days. The method of the disclosure involves no stimulant. The tobacco leaves are incubated in a sealed container at a fixed temperature, for example, 37° C., for 10-12 hours and then treated for alkaloids extraction and data analysis. The method of the disclosure simplifies the alkaloids extraction process and compresses the operation time.

2. The method of the disclosure uses a GC-MS to quantify the content of nicotine and nornicotine. The process including alkaloids extraction and instrument analysis takes only 5-6 minutes, thus saving the analysis time.

3. The method of the disclosure introduces PPNC as an alternative indicator to identify the converters. PPNC is easier to obtain than PNC, and is unaffected by the factors such as the purity of the standard sample and the accuracy of the calibration curve.

DETAILED DESCRIPTION

Figure 1:
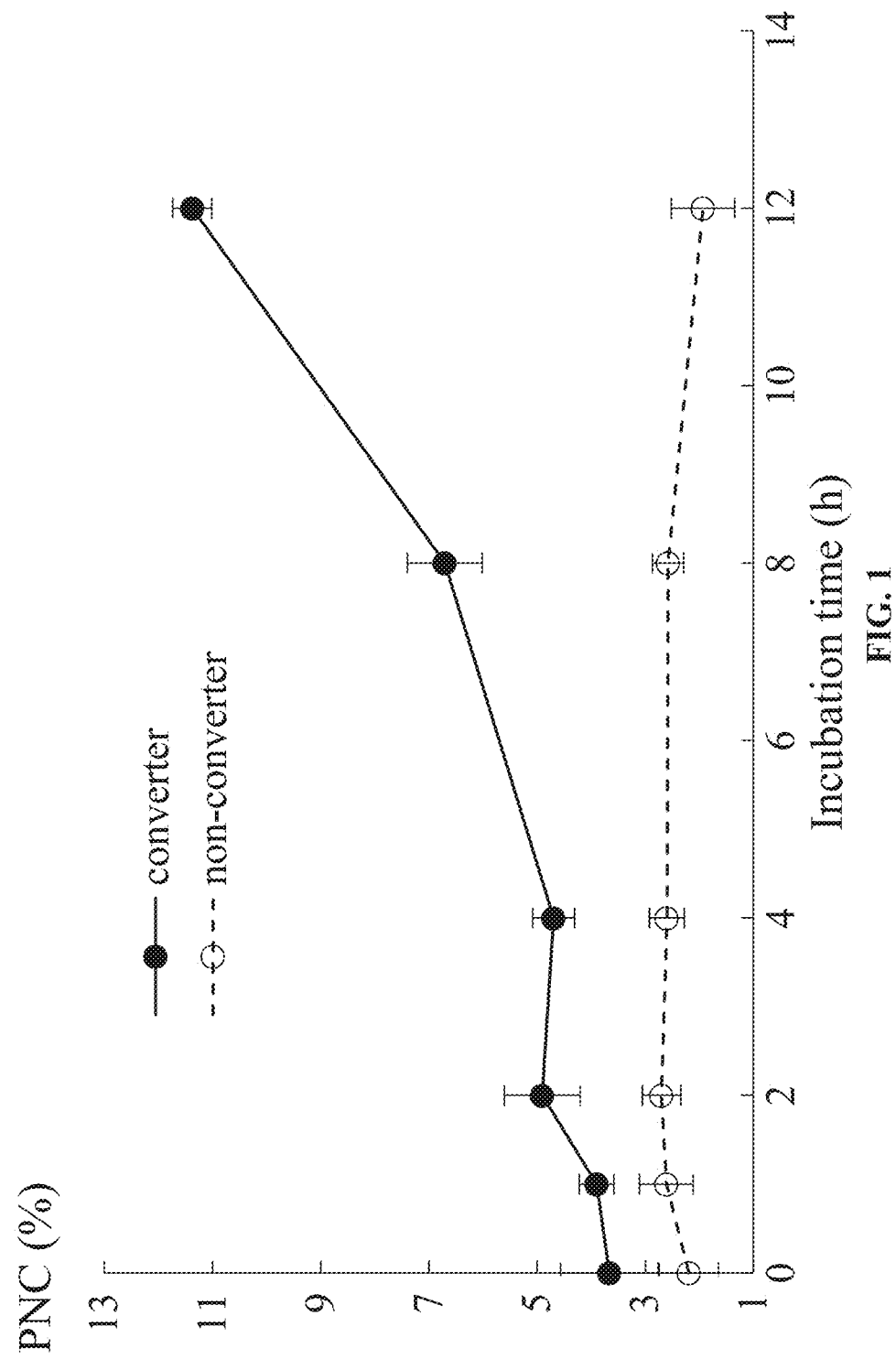
FIG. 1 shows the influence of incubation time for the PNC-based discrimination of converters and non-converters.

To further illustrate the disclosure, embodiments detailing a method for identifying nicotine converters are described below. It should be noted that the following embodiments are intended to describe and not to limit the disclosure.

The disclosure provides a method for identifying nicotine converters of tobacco plants, the method comprising: leaf sampling, sample incubation, alkaloid extraction, instrumental analysis, and data analysis.

Specifically, the method comprises:

S1. Leaf sampling: sowing and cultivating tobacco seeds to be identified in a greenhouse tray for 45-55 days; sampling a plurality of leaf disks from each of 45-55 days old seedlings, where the plurality of leaf disks is identical to each other in size and shape:

S2. Sample incubation: incubating the plurality of leaf disks of each seedling in a sealed container at 37° C. for 10-12 hours;

S3. Alkaloid extraction: immersing the plurality of incubated tobacco leaves of each seedling in an extractant, extracting alkaloids and obtaining an extract of each seedling;

S4. Instrumental analysis: analyzing the amounts of nicotine and nornicotine in the alkaloids extract of each seedling by using a gas chromatography-mass spectrometry (GC-MS);

S5. Data analysis: automatically recognizing peaks of nicotine and nornicotine using a GC-MS chemical workstation, calculating an integral of peak areas of the peaks, and calculating the percent nicotine conversion (PNC) and the pseudo percent nicotine conversion (PPNC) as follows:

$$PNC = \frac{C_{nornicotine}}{C_{nicotine} + C_{nornicotine}};$$

$$PPNC = \frac{A_{nornicotine}}{A_{nicotine} + A_{nornicotine}};$$

where C represents the concentration of nicotine or nornicotine, and A represents the peak area of nicotine or nornicotine; wherein when the PNC or PPNC of a seedling is greater than or equal to a threshold value, the seedling is identified as a converter and removed from the tobacco plant; otherwise, the seedling is identified as a non-converter and retained.

In S5, the threshold value for the PNC is 9%, and the threshold value for the PPNC is 1.6%.

Sampling a plurality of leaf disks from each seedling comprises: folding a leaf of each seedling in half twice along a main vein of the leaf; evenly punching each folded leaf for 2-4 times by using a 5-7 mm hole punch, and collecting 8-16 circular disks of the leaf.

In S1, the product of length and width of the leaf to be folded of each seedling is greater than 35 cm$^2$.

In S3, the extractant is methyl tert-butyl ether (MTBE); the circular disks of the leaf are transferred to a 1.5-mL centrifuge tube comprising 0.3 mL MTBE, 1 μg/mL quinolone, and 0.5 mL 2.5% NaOH aqueous solution; the mixture in the centrifuge tube is vortexed for 1 minute: the mixture is suspended for phase separation, and 150 μL of the supernatant is transferred to a GC-MS vial for instrumental analysis. The main reason for choosing MTBE as the extractant is because MTBE and water have different polar properties; nicotine and nornicotine are dissolved better in MTBE than in aqueous alkali. There is no emulsification occurs and the organic phase separates quickly from the aqueous alkali in the process of extraction.

In S4, the GC-MS is Agilent 7890A-5977B.

In S4, the GC analysis of the GC-MS is performed under the following conditions: a DB-5 MS capillary column is employed, the split ratio is set as 10:1, the injection volume is 2 μL, and the chromatographic separation at the temperature of 270° C. for 1.8 minutes: the total execution time for each sample is 3.4-3.6 min, and the flow rate of the carrier gas of the column is 1.5-mL/min. The disclosure employs an analytical method that combines features of gas chromatography and mass spectrometry to promote separation of the samples. The chromatographic analysis is performed without complete separation of the compounds to be test. So, the separation process can be carried out in a constant temperature mode, instead of a temperature programmed mode. The constant temperature mode is much time-conserving than the temperature programmed mode that heats or cool to a setpoint temperature within a certain period of time. The constant temperature mode takes only 1.8 min to separate the compounds to be test, and the total execution time on each sample instrument is 3.4-3.6 min.

In certain embodiments, the carrier gas is helium.

In S4, the MS analysis of the GC-MS is performed under the following conditions: data is collected using a selected ion monitoring (SIM) mode; quantitation ions are m/z 84 for nicotine and m/z 70 for nornicotine; electron ionization (EI) with the energy of 70 eV is employed; the detector voltage is 1.0 kV; the ion source temperature and the transfer line temperature are constant at 200° C. and 300° C., respectively.

In S1, the tobacco plant is flue-cured tobacco or burley tobacco.

To verify the accuracy and feasibility of the method of the disclosure, the following examples are implemented to identity converters from a tobacco seedling population. The tobacco seedling is also cultivated using a conventional method described in the background for comparison. Specifically, the tobacco samples are incubated in a stimulant for 7 days at 37° C. and 80% relative humidity. These samples were analyzed to confirm the classification of the converters and the non-converters.

Example 1

S1. Leaf sampling

The seeds of tobacco cultivar Yunyan 85 were sown and cultivated in a greenhouse tray (9×18 cells total; size of per cell: 3 cm×3 cm). Seedlings were sampled 45 days after sowing. The largest leaf was cut off from each seedling (The area of each largest leaf was greater than 35 cm$^2$ given by the product of its length and width). Each leaf was folded in half along the main vein thereof, and folded again. 12 leaf disks were cut from each tobacco leaf by using a 6 mm hole punch, making sure the leaf disks were uniformly distributed across the surface of each folded leaf. Then the 12 leaf disks were transferred to a 1.5-mL centrifuge tube.

S2. Sample incubating: the leaf disks were incubated in a sealed container at 37° C. for 10 hours. The moisture was maintained by sealing the centrifuge tube.

S3. Alkaloids extraction: MTBE was used as the extractant, and quinoline was used as the internal standard. Three hundred micro litter of MTBE containing 1 μg/mL quinolone, and 0.5 mL 2.5% NaOH aqueous solution were added to the 1.5-mL centrifuge tube containing the circular disks. The mixture was vortexed for 1 minute. The layers were visible immediately after the vortex and 150 μL of supernatant was transferred to a GC-MS vial and submitted for instrumental analysis.

S4. Instrumental analysis: an Agilent 7890A gas chromatograph coupled with a 5977B mass spectrometer was used for instrumental analysis. For GC separation, a DB-5 MS capillary column (30 m×0.25 mm×0.25 μm) with split ratio of 20:1 and injection volume of 2 μL were applied. The column temperature was kept at 270° C. for 1.8 minutes for alkaloids separation. The total execution time for each sample was 3.5 min. The gas (helium) flow was fixed as 1.0 mL/min. the MS data was collected using a selected ion monitoring (SIM) mode. Quantitation ions were m/z 84 for nicotine and m/z 70 for nornicotine. Electron ionization with the energy of 70 eV was applied. The detector voltage was 1.0 kV. The temperature of the ion source and the transfer line were held constant at 200° C. and 300° C., respectively.

S5. Data analysis: the automated peak recognition and integration for nicotine and nornicotine were carried out using the MSD ChemStation F.01.03.2357 (Agilent technologies). The integration was manually checked for errors, and was allowed to execute once more if necessary. The concentration ranges of nicotine and nornicotine used in the calibration curve were 0.78-50 μg/mL and 0.15-10 μg/mL, respectively, and the concentration of the internal standard (quinoline) was 1.0 μg/mL. Quantitative calibration was performed using MSD ChemStation. All the data obtained was imported into a Microsoft Excel worksheet. PNC was used to distinguish converters and non-converters:

$$PNC = \frac{C_{nornicotine}}{C_{nicotine} + C_{nornicotine}};$$

where C represents the concentration (mol/L) of nicotine or nornicotine. The tobacco seedling was identified as a converter and removed when the PNC was greater than or equal to 10%. Compared with the method in the related art, the converter can be removed completely without milling, weighting, or long-time incubating the leaves.

Example 2

Example 2 is basically the same as that in Example 1, except use of PPNC to distinguish the converters from the seedling population. The tobacco seedling was identified as a converter and removed when the PPNC was greater than or equal to 1.8%. Compared with the method in the related art, the converter can be removed completely without milling, weighting, or long-time incubating the leaves.

Example 3

S1. Leaf Sampling

The seeds of burley tobacco TN90 were sown and cultivated in a greenhouse tray (9×18 cells total: size of per cell: 3 cm×3 cm). Seedlings were sampled 45 days after sowing. The largest leaf (The area of each largest leaf was greater than 35 cm² given by the product of its length and width) of each seedling was cut off the product of. Each leaf was folded in half along the main vein, and folded again. Twelve leaf disks were cut from each tobacco leaf by using a 5 mm hole punch, making sure the leaf disks are uniformly distributed across the surface of each folded leaf. Then the leaf disks were transferred to a 1.5-mL centrifuge tube.

S2. Sample incubation: the leaf disks were incubated in a sealed container at 37° C. for 10 hours. The moisture was maintained by sealing the centrifuge tube.

S3. Alkaloids extraction: MTBE was used as an extractant, and quinoline was used as the internal standard. 0.3 mL of MTBE containing 1 μg/mL quinolone, as well as 0.5 mL 2.5% NaOH aqueous solution were added to the 1.5-mL centrifuge tube containing the circular disks. The mixture was vortexed for 1 minute and diluted with a solvent. The layers were visible immediately after the vortex and 150 μL of supernatant was transferred to a GC-MS vial and submitted for instrumental analysis.

S4. Instrumental analysis: an Agilent 7890A gas chromatograph coupled with a 5977B mass spectrometer was used for instrumental analysis. For GC separation, a DB-5 MS capillary column (30 m×0.25 mm×0.25 μm) with split ratio of 20:1 and injection volume of 2 μL were applied. The column temperature was kept at 270° C. for 1.8 minutes for alkaloids separation. The total execution time for each sample was 3.5 min. The gas (helium) flow was fixed as 1.0 mL/min. the MS data was collected using a selected ion monitoring (SIM) mode. Quantitation ions were m/z 84 for nicotine and m/z 70 for nornicotine. Electron ionization with the energy of 70 eV was applied. The detector voltage was 1.0 kV. The temperature of the ion source and the transfer line were held constant at 200° C. and 300° C., respectively.

S5. Data analysis: the automated peak recognition and integration for nicotine and nornicotine were carried out using the MSD ChemStation F.01.03.2357 (Agilent technologies). The integration was manually checked for errors, and was allowed to execute once more if necessary. The concentration ranges of nicotine and nornicotine used in the calibration curve were 0.78-50 μg/mL and 0.15-10 μg/mL, respectively, and the concentration of the internal standard (quinoline) was 1.0 μg/mL. Quantitative calibration was performed using MSD ChemStation. All the data obtained was imported into a Microsoft Excel worksheet. PNC was used to distinguish converters and non-converters:

$$PNC = \frac{C_{nornicotine}}{C_{nicotine} + C_{nornicotine}};$$

where C represents the concentration (mol/L) of nicotine or nornicotine. The tobacco seedling was identified as a converter and removed when the PNC was greater than or equal to 9%. Compared with the method in the related art, the converter can be removed completely using the method without hurting the non-converter.

Example 4

Example 4 is basically the same as that in Example 3, except for the use of PPNC to distinguish converters from the seedling population. The tobacco seedling is identified as a converter and removed when the PPNC is greater than or equal to 1.6%.

Compared with the method in the related art, the converter can be removed completely without milling, weighting, long-time incubating, or chemical standard curves construction for absolute quantitation.

Example 5

Example 5 takes flue-cured tobacco Yunyan 85 as an example.

1. Stability Assessment of the Sampling

The weighing step was omitted from the sampling process in Example 5 to rapidly identify the converters. The weight stability of the collected disk samples was evaluated (as shown in Table 1) and the result indicates that the relative standard deviation (RSD) of weights among 10 different tobacco leaf samples is between 4.1-4.6%, which means that the sampling method can collect leaf samples with stable weight. The reason for the desired result may be ascribed as the same growing environment of the tobacco seedlings, which result in the same thickness and density of leaves. The stability of the sample weight ensures the comparability of the PNC or PPNC.

TABLE 1

Weight distribution of the leaf samples cut out by a hole punch

|  | Leaf area (cm$^2$) | Leaf weight (mg) | RSD (%) |
|---|---|---|---|
| Converter | 68.1 ± 12.3 | 46.1 ± 2.1 | 4.6 |
| Non-converter | 69.3 ± 13.2 | 46.0 ± 1.9 | 4.1 |

Note:
Leaf area is the average leaf area of 10 samples, where the area of each sample is given by the product of the length and the width. RSD is the relative standard deviation of the sample weight. Both the converter and the non-converter are flue-cured tobacco plants.

2. Effect of Punch Position on the Analysis Result

To rapidly identify the converter, 12 leaf pieces of one leaf were cut off as a sample, instead of using the whole leaf or the whole plant as a sample. This assay compares the difference between the samples obtained from the edge and the middle of one seedling leaf (as shown in Table 2). The results show that the edge contains higher contents of nicotine and nornicotine than that the middle. But the PNC and PPNC of the edge are not significantly different from those of the middle. The difference indicates that the punch position has only small effect on the PNC and PPNC, while it is still recommended to sample at the same position on each leaf. For example, in this assay, the punch positions are uniformly distributed over the surface of each folded leaf.

TABLE 2

Comparison of sampling positions on a leaf

|  | Punch position | Nicotine (µg/g) | Nornicotine (µg/g) | PNC (%) | PPNC (%) |
|---|---|---|---|---|---|
| Converter | edge | 166.8 ± 36.7 | 8.0 ± 1.7 | 5.1 ± 1.3 | 1.1 ± 0.3 |
|  | middle | 132.9 ± 24.0 | 6.7 ± 1.0 | 5.3 ± 0.4 | 1.1 ± 0.1 |
| Non-converter | edge | 173.3 ± 22.7 | 2.8 ± 0.3 | 1.8 ± 0.3 | 0.3 ± 0.1 |
|  | middle | 132.4 ± 17.9 | 2.7 ± 0.3 | 2.2 ± 0.3 | 0.4 ± 0.1 |

Note:
the leaves for the data in Table 2 were not incubated.

3. Effect of Leaf Size on PNC and PPNC

Table 3 shows a comparative analysis of the effect of leaf size on PNC and PPNC on 45-day-old flue-cured tobacco seedlings. The results show that there is no significant difference (p>0.05) on the contents of nicotine and nornicotine between large leaves and small leaves, and so is the difference between PNC and PPNC. Considering that it is difficult to obtain needed leaf disks from a very small leaf, it is recommended to sample the leaves with a leaf area of greater than 35 cm$^2$ given by the product of its length and width.

TABLE 3

Effect of leaf size on PNC and PPNC

|  |  | Leaf area (cm$^2$)$^a$ | Nicotine (µg/g) | Nornicotine (µg/g) | PNC (%) | PPNC (%) |
|---|---|---|---|---|---|---|
| Converter | Large leaf | 114.1 ± 23.9 | 145.3 ± 43.6 | 6.4 ± 2.9 | 4.7 ± 1.6 | 0.9 ± 0.4 |
|  | Small leaf | 43.4 ± 9.1 | 128 ± 42.4 | 7.7 ± 2.3 | 6.6 ± 2.7 | 1.4 ± 0 6 |
| Non-converter | Large leaf | 113.4 ± 38.4 | 185.2 ± 26.3 | 2.7 ± 0.3 | 1.6 ± 0.5 | 0.3 ± 0.1 |
|  | Small leaf | 42.5 ± 15.6 | 230.5 ± 39.8 | 3.0 ± 1.0 | 1.4 ± 0.6 | 0.2 ± 0.1 |

Note:
Leaf area is given by the product of length and width.

4. Effect of Stimulants on the Conversion of Nicotine

The existing technology promotes the conversion of nicotine with stimulants such as ethylene, ethephon, and sodium bicarbonate, in which the sodium carbonate is believed to have the same stimulating effect with ethylene and ethephon. The assay performed for the converter seedlings treated with and without 0.8% sodium bicarbonate indicates that there is no significant difference in PNC values between these two treatments. Therefore, no stimulant was added during the incubating process of the disclosure.

5. Distribution of PNC and PPNC in Incubated Tobacco Samples

Figure 2:
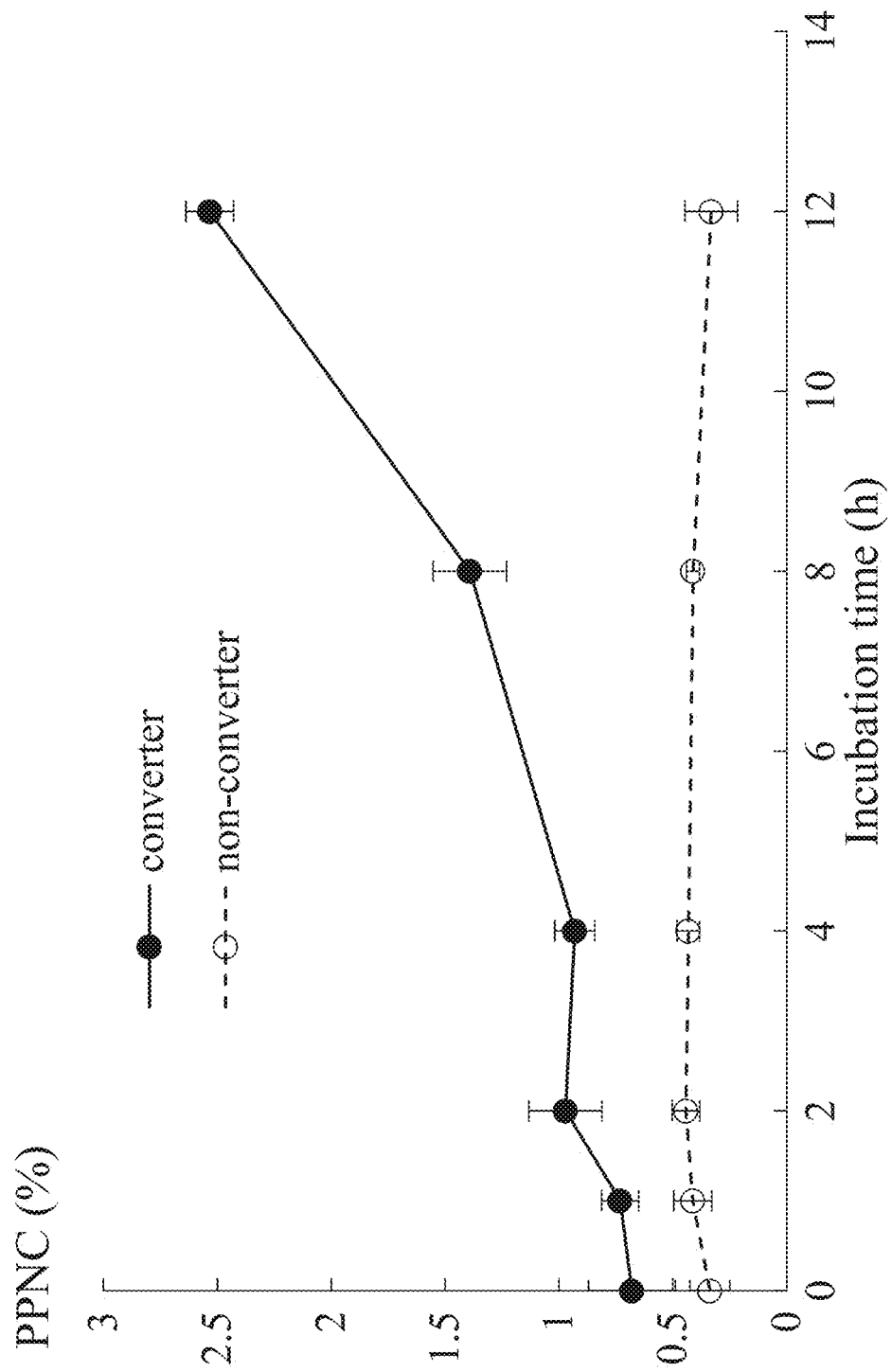
FIG. 2 shows the influence of incubation time for the PPNC-based discrimination of converters and non-converters.
Figure 3:
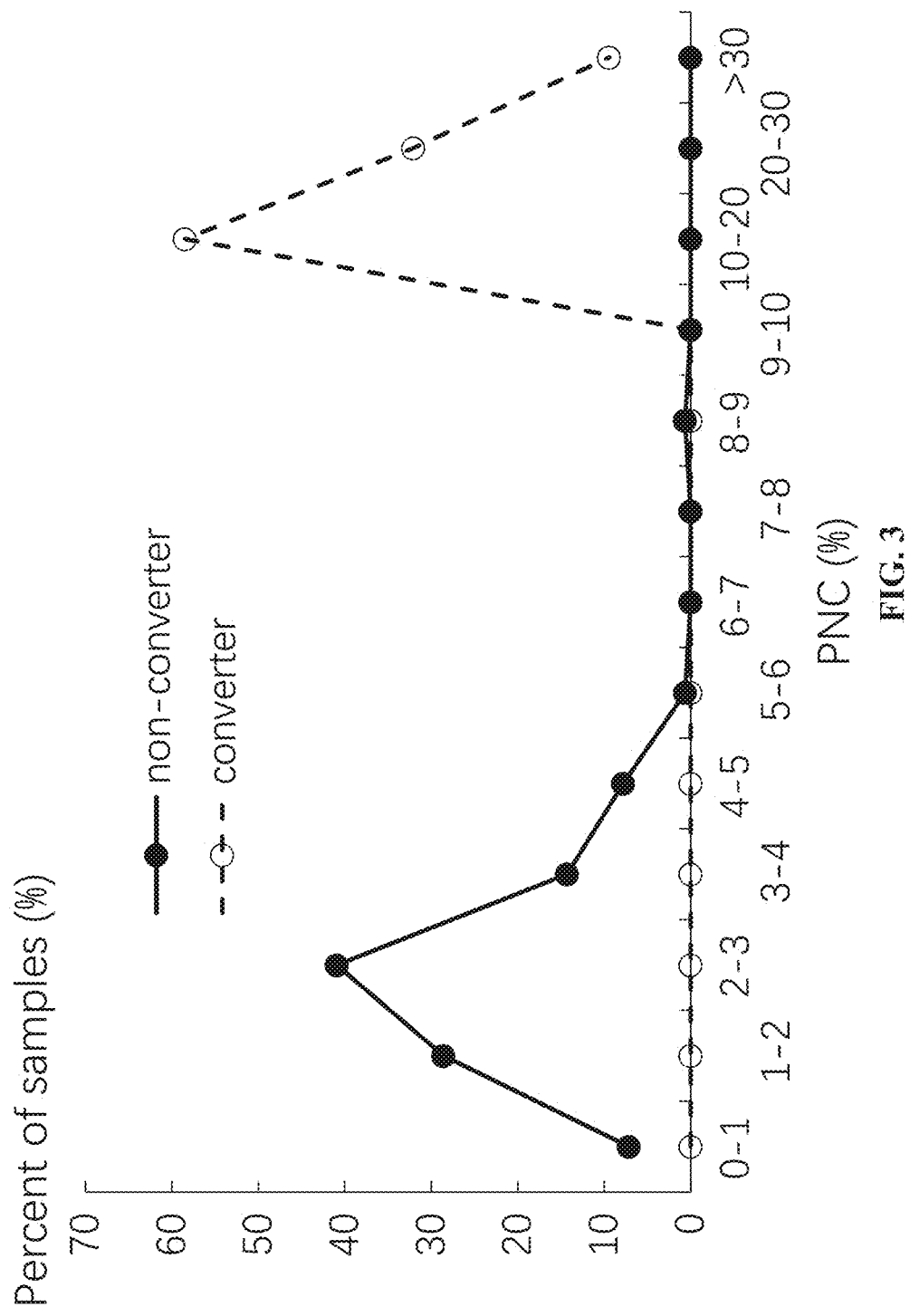
FIG. 3 is a distribution diagram of the PNC between converters and non-converters.
Figure 4:
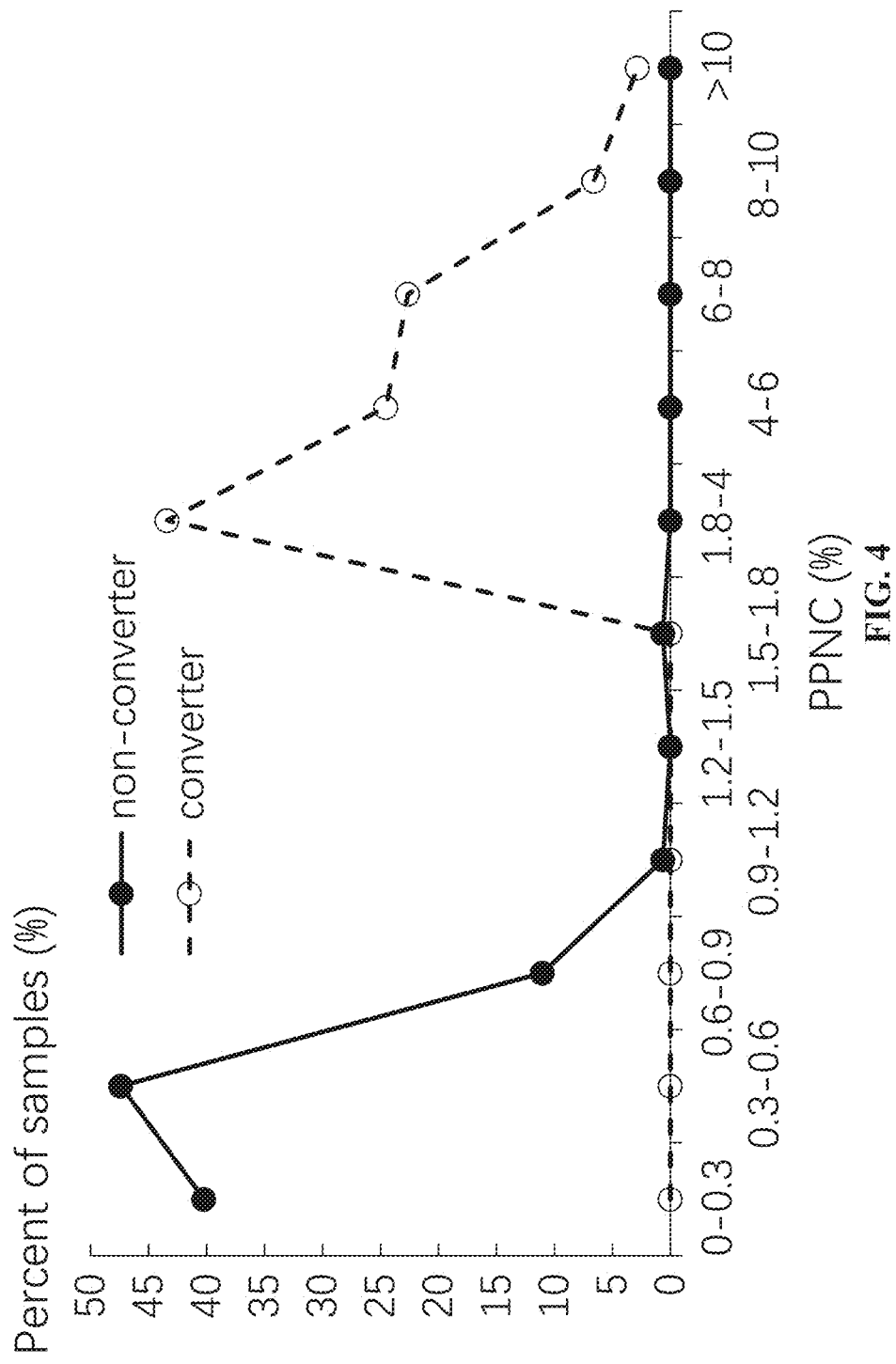
FIG. 4 is a distribution diagram of the PPNC between converters and non-converters.
Figure 5:
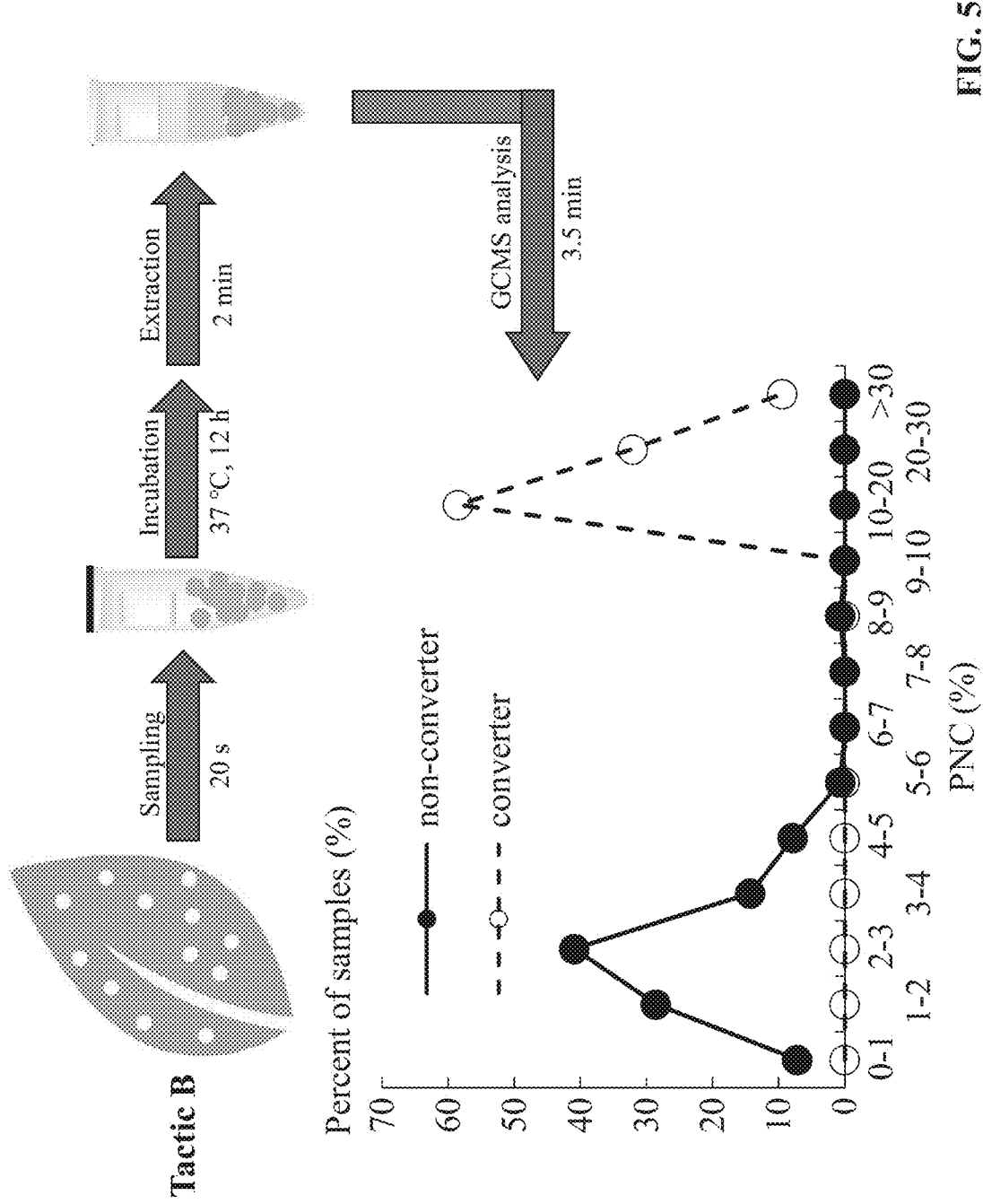
FIG. 5 is a flow chart of a method for identifying nicotine converters of tobacco plants of the disclosure.

As shown in FIGS. 1 and 2, the tobacco leaf samples (sealed in a 1.5-mL centrifuge tube) that has been collected were incubated at 37° C. for 12 hours. The PNC and PPNC respectively increased by 3.1 times and 3.7 times in the converters, while no significant changes for the non-converters was discovered. This indicates that the incubating process promotes the conversion of nicotine to nornicotine of the converters, so that the PNC or PPNC of the converter and non-converter no longer overlap (as shown in FIGS. 3 and 4). The converters are completely removed without losing non-converters by using values of PNC or PPNC as the decider.

After the incubation, the average PNC and PPNC of the seedling converters are 3.1 and 3.7 times that of the non-converters, respectively. The method of the disclosure eliminates the sample grinding and weighing step, as well as the steps of adding stimulants and controlling the humidity using specified instruments for the incubation of tobacco leaves. The method of the disclosure simplifies the measurement of nicotine and nornicotine, eliminates the sample grinding and sample weighing steps, shortens the sample extraction time, and optimizes the GC-MS analysis method (using a constant temperature mode at 270° C. instead of a programmed temperature mode). Therefore, the identification without incubation takes just 5-6 minutes (as shown in FIG. 4).

It will be obvious to those skilled in the art that changes and modifications may be made, and therefore, the aim in the appended claims is to cover all such changes and modifications.

What is claimed is:

1. A method, comprising:
   1) sowing and cultivating tobacco seeds to be identified in a greenhouse tray for 45-55 days; sampling a plurality of leaf disks from each of 45-55 days old seedlings of the tobacco plant, where the plurality of leaf disks is identical to each other in size and shape;
   2) incubating the plurality of leaf disks of each seedling in a sealed container at 37° C. for 10-12 hours, thereby obtaining a plurality of incubated tobacco leaves of each seedling;
   3) immersing the plurality of incubated tobacco leaves of each seedling in an extractant, extracting alkaloids and obtaining an extract of each seedling;
   4) analyzing the amounts of nicotine and nornicotine in the alkaloids extract of each seedling by using a gas chromatography-mass spectrometry (GC-MS); and
   5) automatically recognizing peaks of the alkaloids extract of each seedling and a standard sample using a GC-MS chemical workstation, calculating an integral of peak areas of the peaks, and calculating a percent nicotine conversion (PNC) and a pseudo percent nicotine conversion (PPNC) as follows:

$$PNC = \frac{C_{nornicotine}}{C_{nicotine} + C_{nornicotine}};$$

$$PPNC = \frac{A_{nornicotine}}{A_{nicotine} + A_{nornicotine}};$$

where C represents a concentration (mol/L) of nicotine or nornicotine, and A represents a peak area of nicotine or nornicotine; when the PNC or PPNC of a seedling is greater than or equal to a threshold value, the seedling is identified as a converter and removed from the tobacco plant; otherwise, the seedling is identified as a non-converter and retained.

2. The method of claim 1, wherein in 5), the threshold value for the PNC is 9%, and the threshold value for the PPNC is 1.6%.

3. The method of claim 1, wherein in 1), sampling a plurality of leaf disks from each seedling comprises: folding a leaf of each seedling in half twice along a main vein of the leaf; evenly punching each folded leaf for 2-4 times by using a 5-7 mm hole punch, and collecting 8-16 circular disks of the leaf.

4. The method of claim 3, wherein in 1), a product of length and width of the leaf to be folded of each seedling is greater than 35 cm$^2$.

5. The method of claim 3, wherein in 3), the extractant is methyl tert-butyl ether (MTBE); the circular disks of the leaf are transferred to a 1.5-mL centrifuge tube comprising 0.3 mL MTBE, 1 µg/mL quinolone, and 0.5 mL 2.5% NaOH aqueous solution; a mixture in the centrifuge tube is vortexed for 1 minute; the mixture is suspended for layer separation, and 150 µL of a supernatant is transferred to a GC-MS vial for instrumental analysis.

6. The method of claim 1, wherein in 4), GC analysis of the GC-MS is performed under the following conditions: a DB-5 MS capillary column is employed, a split ratio is set as 10:1, an injection volume is 2 µL, and chromatographic separation is performed at a temperature of 270° C. for 1.8 minutes; a flow rate of a carrier gas in the column is 1.5-mL/min, and a total execution time for each sample is 3.4-3.6 min.

7. The method of claim 6, wherein the carrier gas is helium.

8. The method of claim 1, wherein in 4), MS analysis is performed under the following conditions: data is collected using a selected ion monitoring (SIM) mode; quantitation ions are m/z 84 for nicotine and m/z 70 for nornicotine; electron ionization (EI) with an energy of 70 eV is employed; a detector voltage is 1.0 kV; a temperature of an ion source and a transfer line are set as 200° C. and 300° C., respectively.

9. The method of claim 1, wherein the tobacco plant is flue-cured tobacco or burley tobacco.

10. The method of claim 2, wherein the tobacco plant is flue-cured tobacco or burley tobacco.

11. The method of claim 3, wherein the tobacco plant is flue-cured tobacco or burley tobacco.

12. The method of claim 4, wherein the tobacco plant is flue-cured tobacco or burley tobacco.

13. The method of claim 5, wherein the tobacco plant is flue-cured tobacco or burley tobacco.

14. The method of claim 6, wherein the tobacco plant is flue-cured tobacco or burley tobacco.

15. The method of claim 7, wherein the tobacco plant is flue-cured tobacco or burley tobacco.

16. The method of claim 8, wherein the tobacco plant is flue-cured tobacco or burley tobacco.

* * * * *